United States Patent [19]

Marcantonio et al.

[11] Patent Number: 5,113,454
[45] Date of Patent: May 12, 1992

[54] FORMATION TESTING WITH DIGITAL IMAGE ANALYSIS

[75] Inventors: Jeffrey J. Marcantonio; Christopher W. Jones, both of South Glens Falls, N.Y.

[73] Assignee: Kajaani Electronics Ltd., Kajaani, Finland

[21] Appl. No.: 234,478

[22] Filed: Aug. 19, 1988

[51] Int. Cl.⁵ .............................................. G06K 9/36
[52] U.S. Cl. ................................. 382/27; 382/28; 382/52; 358/106; 356/237
[58] Field of Search ................. 382/50, 51, 52, 27, 382/28, 8, 1; 358/106; 250/562, 563; 356/237

[56] References Cited

U.S. PATENT DOCUMENTS

| | | | |
|---|---|---|---|
| 3,389,789 | 6/1968 | Watson et al. | 358/106 |
| 4,139,306 | 2/1979 | Norton | 358/106 |
| 4,196,454 | 4/1980 | Warren | 382/52 |
| 4,254,400 | 3/1981 | Yoda et al. | 382/50 |
| 4,402,604 | 9/1983 | Nash | 356/237 |
| 4,428,672 | 1/1984 | Allard et al. | 356/237 |
| 4,454,542 | 6/1984 | Miyazawa | 358/106 |
| 4,724,481 | 2/1988 | Nishioka | 358/106 |
| 4,903,316 | 2/1990 | Mongo et al. | 382/50 |

OTHER PUBLICATIONS

The New Artek AUTOCOUNT Brochure by Artek Systems Corporation "Automatic Image Analysis and Measurement Systems for the Pulp and Paper Industry", by Optomax, Inc.

Primary Examiner—David K. Moore
Assistant Examiner—Yon Jung
Attorney, Agent, or Firm—Nixon & Vanderhye

[57] ABSTRACT

A system is disclosed which increases the level of accuracy and precision for quantifying formations in paper. A CCD camera is used to capture data from a large portion of the paper. A diffuse illumination source is used to back light the paper sample. A microcomputer uniquely analyzes digitized image data. In this regard, after the image is stored in memory, a two-dimensional window is created and scanned over the entire frame to two-dimensionally analyze the image intensity level data. Average window intensity levels are generated that are compared to one another. In this regard, smaller local pixel variations are compared to these windows giving both regional and local variation data. Hundreds of thousands of data points are considered in these comparisons which are divided into sixty four difference levels. An array of 64 sample intervals are compiled, each representative of the number of accumulated data points that, when compared to their neighboring region, differ in intensity level by a percentage of the total mean intensity of the entire sample area. An index is generated that accurately reflects the gradient or rate of change over the sample sheet in two dimensions.

32 Claims, 4 Drawing Sheets

FORMATION TESTING WITH DIGITAL IMAGE ANALYSIS

FIELD OF THE INVENTION

This invention relates generally to digital image analysis. More particularly, the invention relates to a method and apparatus for digital image analysis for measuring the properties of a medium such as paper to detect the presence of non-uniformities, e.g., thin spots, pin holes, dirt specks, etc. The present invention uses a microcomputer based system to uniquely analyze and process data captured from a CCD camera to generate an index defining the uniformity of the medium under test.

BACKGROUND AND SUMMARY OF THE INVENTION

Paper is typically formed by spraying pulp fibers onto a web and allowing the pulp to dry. This process results in the random distribution of the pulp fibers sprayed on the web. Thus, on certain portions of the web, the fibers tend to clump together forming what is referred to in the paper industry as flocs, while voids are left on other portions of the web.

Such flocs and voids may be readily observed by holding the paper product up to, for example, a fluorescent light source. Dark and light formations on the paper may be observed which correspond to the flocs and voids, respectively. Other "formations" in the paper may be due to dirt specks, pin holes, etc. As used herein a "formation" in paper or any other medium refers to the physical distribution or orientation of fibers and other solid constituents in the structure of the medium which effects its appearance and other physical properties.

The uniformity of the distribution of the fibers in a paper product significantly impacts its physical properties. In this regard, uniformity directly impacts the strength properties of the paper, the paper's printability, how well the paper will run on particular printing machines, etc. Accordingly, paper manufacturers have a dire need to receive accurate data regarding the nature of such formations or non-uniformities as early as possible in the paper manufacturing process.

Typically, a paper manufacturer has a test sheet analyzed in a laboratory. The testing process is designed to determine whether the formations present in the test sheet are such that the current run of paper is acceptable for the application for which it is designed. In this regard, paper targeted for use by a magazine must have a very high degree of uniformity, whereas paper utilized to form a sandwich bag only requires a relatively low degree of uniformity.

In the prior art, in order to quantitatively analyze the formations in paper, one typical approach is to measure data points across a predetermined portion of the paper, one spot at a time. In this regard, an illuminated web of paper secured, for example, to a drum is scanned by a single photocell which measures the optical density of the paper. Such a system tends to be inherently inaccurate due, for example, to fluctuations in the light source at the sequential data points or variations introduced by drum vibrations.

Moreover, using such a prior art system, if the same run of paper were tested on different testing units of the same design substantially different readings would often result, e.g., a 10% difference in the readings. Accordingly, if the same type of testing device were to be used at different paper mills, the fact that the devices yielded approximately the same reading, would not guarantee that the quality of the paper produced at each mill is identical or that the paper produced at each mill would be acceptable for the same application.

One currently available system for formation testing uses a camera to obtain a two-square inch sample of data points from paper illuminated by a non-adjustable, fluorescent light source. The captured data is analyzed by a microcomputer. Even though this system is menu driven, unlike the present invention, it requires a skilled operator trained in digital image analysis to utilize.

Additionally, as noted above, this system selects data points from a small field of view, i.e., 2 square inches. This field of view may not be adequate to accurately quantitatively analyze the fibrous bundles in paper. In this regard, by only looking at a limited area of the paper, this system does not access a representative sample of the fiber distribution.

Other characteristics of this system also contribute to its inability to achieve highly accurate results. For example, it does not include an adjustable light source which compromises the accuracy of its test results. Additionally, this system has difficulties producing accurate results with samples which include thin spots, pin holes, or dirt specks.

The method and apparatus of the present invention serve to increase the level of accuracy and precision for quantifying formations in paper. The present invention through the use of a CCD camera simultaneously captures data from a large portion of the paper. In this fashion, the data retrieved is more likely to accurately reflect the quality of the paper rather than transient environmental conditions which affected the aforementioned single point photodetecting system. The present invention digitizes the image data captured by the CCD camera and utilizes a microcomputer to uniquely analyze the data to create an index of the non-uniformity of the optical light transmission through the sample over its entire area.

The present invention utilizes a diffuse illumination source with which to back light the paper sample. An incandescent light source is focused to cover an area larger than the anticipated field of view. The light source includes two levels of diffusing material to achieve the most even diffusion of the incandescent lamps source possible. To enhance the accuracy of the sample test data, the microcomputer executes a routine which records a reference image of the illumination surface and ratiometrically compares it pixel for pixel with the actual image of the sample to be processed. By subtracting out these differences, a compensated image of the paper sample is produced.

Thereafter, the microcomputer uniquely analyzes the compensated image data. In this regard, after the compensated image is stored in memory, a two-dimensional window is created and scanned over the entire frame to two-dimensionally analyze the image intensity level data. Average window intensity levels are generated that are compared to one another. In this regard, smaller local pixel variations are compared to these windows giving both regional and local variation data. Hundreds of thousands of data points are considered in these comparisons which are divided into sixty four difference levels. Each difference level is separated by approximately one percent of a 256 level grey scale.

In this fashion, an array of 64 sample intervals are compiled, each representative of the number of accumulated data points that, when compared to their neighboring region, differ in intensity level by a percentage of the total mean intensity of the entire sample area. An index is generated that accurately reflects the gradient or rate of change over the sample sheet in two dimensions. If desired, the user can select a report where the data is pictorially represented in a histogram.

BRIEF DESCRIPTION OF THE DRAWINGS

These as well as other objects and advantages of this invention will be better appreciated by reading the following detailed description of the presently preferred exemplary embodiment taken in conjunction with the accompanying drawings of which.

DETAILED DESCRIPTION OF THE DRAWINGS

Figure 1:
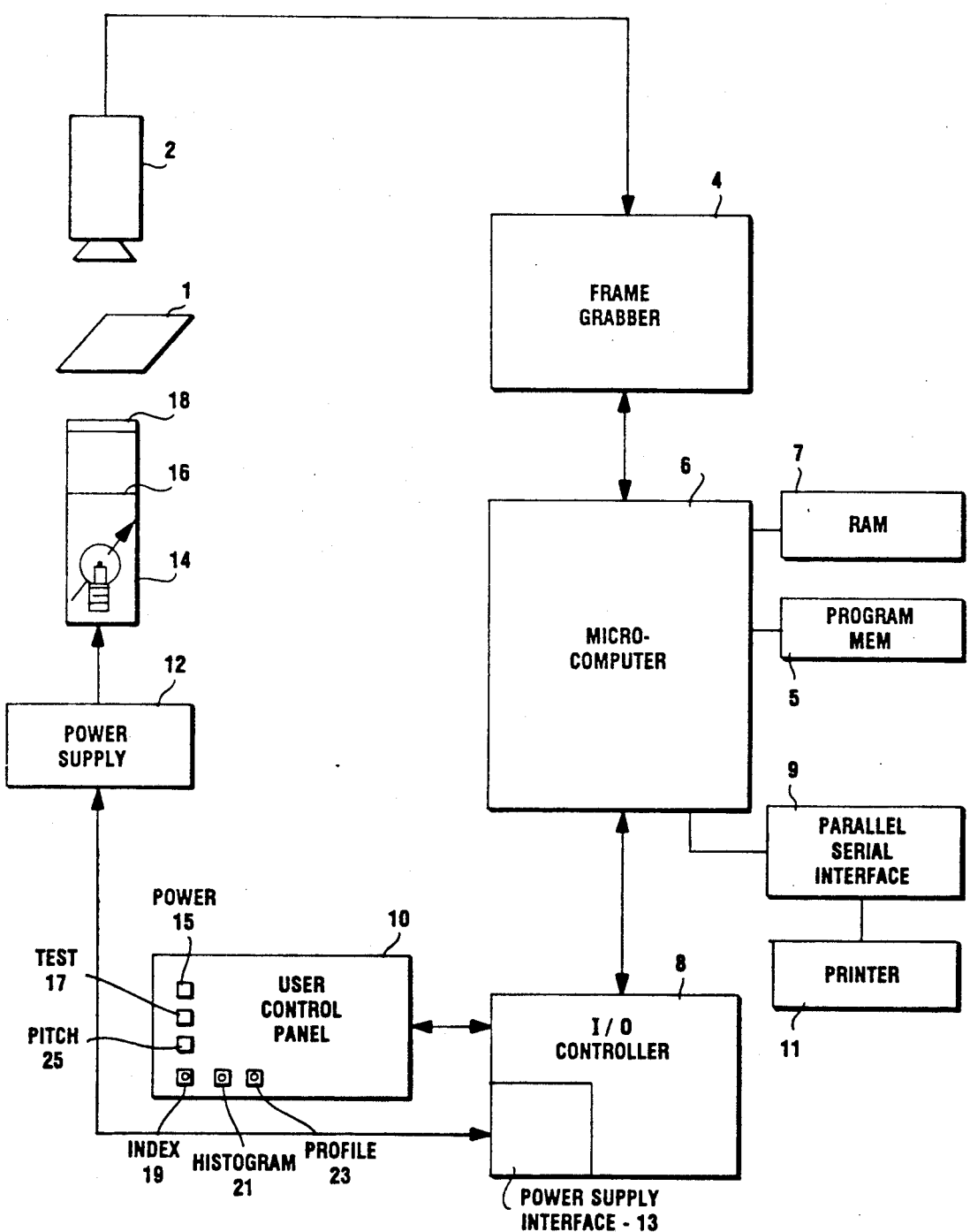
FIG. 1 shows an exemplary embodiment of the formation testing image analysis apparatus of the present invention.

FIG. 1 shows an exemplary embodiment of the formation testing image analysis apparatus of the present invention. The image of sample 1 (which may be paper or another medium such as plastic whose "formation" properties are desired to be studied) is captured by camera 2.

Camera 2 is preferably a charge coupled device (CCD) camera, and may, for example, be a Panasonic Model WV-CD 50. The field of view of the camera 2 is preferably six square inches. Camera 2 has a CCD sensor arranged to capture 510 × 492 picture elements (pixels). The camera 2 also includes features such as switch selectable aperture, gamma and automatic gain control settings, as well as add on options such as a remote iris capability. The camera's response closely resembles the human eye with regard to intensity over the color spectrum so that the colors most intense to the eye are also most intense to the camera. Camera 2 is coupled to its own power supply (not shown). Camera 2 is also coupled via a conventional BNC connector to the input of a frame grabber 4.

Frame grabber 4, which may, for example, be the commercially available Coreco Oculus 200, digitizes the picture received from camera 2 into 512 by 480 picture elements. Associated with each pixel are two pieces of information, one representing its location and the other its intensity level.

The scale of intensity level ranges from zero for black to 255 for white. These grey levels, which are uniquely represented by an 8 bit binary code, are separated by a sensitivity of 0.017578 volts per grey level by the frame grabber 4. Thus, with 256 grey levels a resolution is obtained which is several times that of the human eye. Therefore, over approximately the same spectral response, a much higher sensitivity to intensity variation is achievable than with the human eye.

Frame grabber 4 is controllable via microcomputer 6 to perform such operations as grabbing a frame, and moving frames from one of its associated storage locations to another. The frame grabber 4 is capable of storing four images simultaneously under the control of microcomputer 6. The processing capability of the frame grabber 4 relieves the microcomputer 6 of some of its processing burden and thus facilitates higher speed processing.

Microcomputer 6, which is coupled to frame grabber 4, may, for example, be an IBM PC/AT compatible microcomputer. Microcomputer 6 is coupled to an associated random access memory (RAM) 7, which preferably contains 640 K memory locations, and a program memory 5 which may be a static RAM virtual disk.

Upon turning the microcomputer's power on, the program stored in memory 5 (e.g., the formation testing routine) is loaded into the system's main memory 7 where it is executed. In this fashion, the system can operate without a hard disk thereby allowing operation on, for example, a paper mill floor and eliminating any concern over problems of operating a disk drive in such an environment. Also associated with microcomputer 6 is a parallel/serial interface 9 which is utilized to interface with printer 11. Printer 11 may, for example, be a dot matrix printer and is utilized to provide a selected hard copy report as will be described further below.

Microcomputer 6 is also coupled to an I/O controller 8. I/O controller 8 may, for example, be a Micro R&D MW200 interface which serves to transfer data and control signals between user control panel 10 and microcomputer 6 and between the power supply 12 and the microcomputer 6. The user control panel includes control keys (and associated display indicators) 15, 17 for turning power on and initiating a sample test, respectively. Control switches and indicators 19, 21, and 23 control the selection of one of three different formation testing reports which are selectively generated by the system. Control panel 10 also includes a user selectable distance between test points (pitch) selector 25. This control function may be implemented, for example, by a user accessible digital potentiometer.

When a user closes, for example, test control button 17, a test on a sample is initiated. The I/O controller 8 transmits this status to microcomputer 6 which serves to initiate sample testing and to energize a test-in-progress control light associated with test button 17. The I/O controller 8 also detects the state of the report control switches 19, 21, and 23 on the user control panel and energizes the appropriate associated control panel display indicator depending on which report is selected. It is noted that the reports that may be selected by the user include either a formation index value only (19), a full histogram (21), or a profile report (23) as will be described further below.

Power supply unit 12 is adjustable over a range of 4 to 12 volts and may, for example, be a Lamda LDFW-01 power supply, the unit's voltage being adjustable via a voltage adjust potentiometer to give voltages of 4 to 12 volts DC. I/O controller 8 includes an associated power supply interface 13 which responds to a signal from microcomputer 6 to control the output voltage generated by power supply 12 to thereby vary the illumination generated by light source 14 as will be explained further below. The microcomputer 6 generates a two bit signal which is utilized by power supply interface 13 to either ramp the power supply up or ramp it down to vary its generated output voltage to thereby vary the illumination generated by light source 14. The illumination generated by light source 14 is controlled by microcomputer 6 via I/O controller 8 to initialize the system to obtain a mean grey level on the sample to be tested of 128.

Light source 14 is a 12 volt incandescent light source. A reflector is disposed around the light source so as to reflect light towards sample 1. Disposed between the incandescent source and the sample to be examined is a first diffusion material 16 which may, for example, be a frosted glass layer. The frosted glass layer 16 is evenly etched so as to diffuse the light emanating from light source 14. A second diffusion layer 18 is disposed between a first diffusion layer 16 and sample 1 and may comprise white plexiglass. These two levels of diffusion are inserted to achieve the most even diffusion of light possible. Through the use of diffusion material 16 and 18, the sample to be examined is uniformly illuminated across its length and width.

The incandescent light source 14 is a readily controllable source and provides the necessary spectrum of light in a consistent manner. It is noted that fluorescent light sources could not be utilized to form the light source 14 since fluorescent light sources tend to cause paper with added brighteners to give inaccurate results. The highly regulated DC power supply 12 serves to provide a more stable power supply over time then if the lamp was directly powered from an AC source which may tend to be more variant over time.

In accordance with the present invention, the uniformity of the light from the light source 14 is still further improved under the control of microcomputer 6. In this regard, a reference image of the illumination surface without the sample 1 is initially stored. This reference is then ratiometrically compared pixel for pixel with the actual image of the sample to be processed. By subtracting out any differences, a compensated image of the paper sample is left. This processing compensates for the circular patterns of light having slightly varying intensity which typically would be generated by light source 14.

Focussing now on the operation of the system shown in FIG. 1, after the operator turns the system on, before a test sample is present, the system enters into a calibration process, wherein the light source 14 is initially adjusted until a midrange mean reading of 128 grey levels is achieved. On achieving such a reading, the image from CCD camera 2 is digitized by frame grabber 4 and stored in one of the four frame memories contained in the frame grabber 4. In this fashion, the background illumination without the sample to be examined is stored as a compensation reference image.

After storage of the compensation reference image, the user control panel indicates that samples are ready to be tested. For example, the test light associated with test control switch 17, which had been energized during the calibration mode may be de-energized to indicate that the system is no longer in the calibration mode.

The user then places a sample 1 over the illumination source 14. The sample 1 may either be fed totally manually or with the aid of an automatic feed mechanism.

The user then selects the formation report that is desired by closing the appropriate switch 19, 21, or 23 on control panel 10. In this fashion, the user is able to select the level of detail of the formation testing analysis that will be generated in the output report. The user also selects the pitch length that the sample will be moved at the end of the test via pitch control 25. In this fashion, the paper sample is displaced so that subsequent tests are at different points along its length to insure that a representative sample of its formations are examined.

Upon the operator energizing the test switch 17, the illumination from the light source is adjusted so that the illumination is at the 128 grey level setting (i.e., the mid-range illumination point). Once the illumination source is adjusted to the half way point, the image obtained by camera 2 is captured and stored in one of the four frame memories contained in the frame grabber 4. Thereafter, the stored reference image of the illumination surface without the sample is utilized to ratiometrically adjust the stored image of the paper sample to account for the differences in light from the illumination source for the two images. As noted above, the reference image of the illumination surface is compared pixel for pixel with the actual image of the sample to be processed. By subtracting out such differences, a true compensated image of the paper sample is obtained. In this fashion, areas of the background illumination that are non-uniformly light or dark, are adjusted according to a ratio related to the dynamic range of illumination over the whole sample, the adjustment taking place for each pixel in the sample image to thereby generate a fully compensated image for 480 by 512 pixels.

As will be explained in detail in conjunction with the flowchart of FIGS. 2A and 2B, after the compensated image of the paper sample is stored, a two dimensional window is created and scanned over the entire frame. Average window intensity levels are generated that are compared to one another. In this regard, smaller local pixel variations are compared to larger window average intensity data giving both regional and local variation data. Over 200,000 data points are considered in these comparisons which are divided into 64 difference levels. Each difference level is separated by approximately one percent of the grey scale.

In this way, an array of 64 samples intervals are compiled each representative of the number of accumulated data points that, when compared to the neighboring region, differ in intensity level by a percentage of the total mean intensity of the entire sample area. The mean intensity of each sample is controlled such that it is within 0.8 percent of the center of the 64 difference levels. This makes the measurement of the non-uniformity virtually independent of basis weight variations since every sample has the same starting point mean.

In order to focus on formation, the scale is expanded to utilize the full resolution of the 64 difference level bins. After an index is calculated as will be described below, it is then divided by an arbitrary constant to generate an index formation value ranging from approximately 19 to 122. This results in a scale which retains separation between papers having close formations and yet still measures a full range of formations.

Rather than determining a formation index using a simple histogram height divided by weight calculation an abbreviated standard deviation type of calculation is used. This gives higher accuracy and results in repeatability of less than 1 percent of full scale for both single and multiple unit variations. Thus, if a sample is retested, the system generates a formation indication which is within one percent of prior test results.

Figure 2A:
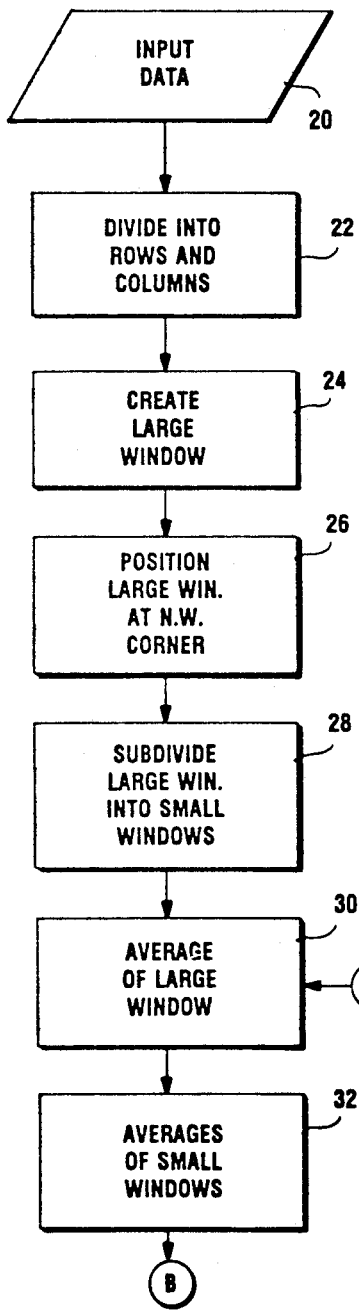
FIGS. 2A and 2B are a flowchart showing how the compensated image data of the paper sample is processed.
Figure 2B:
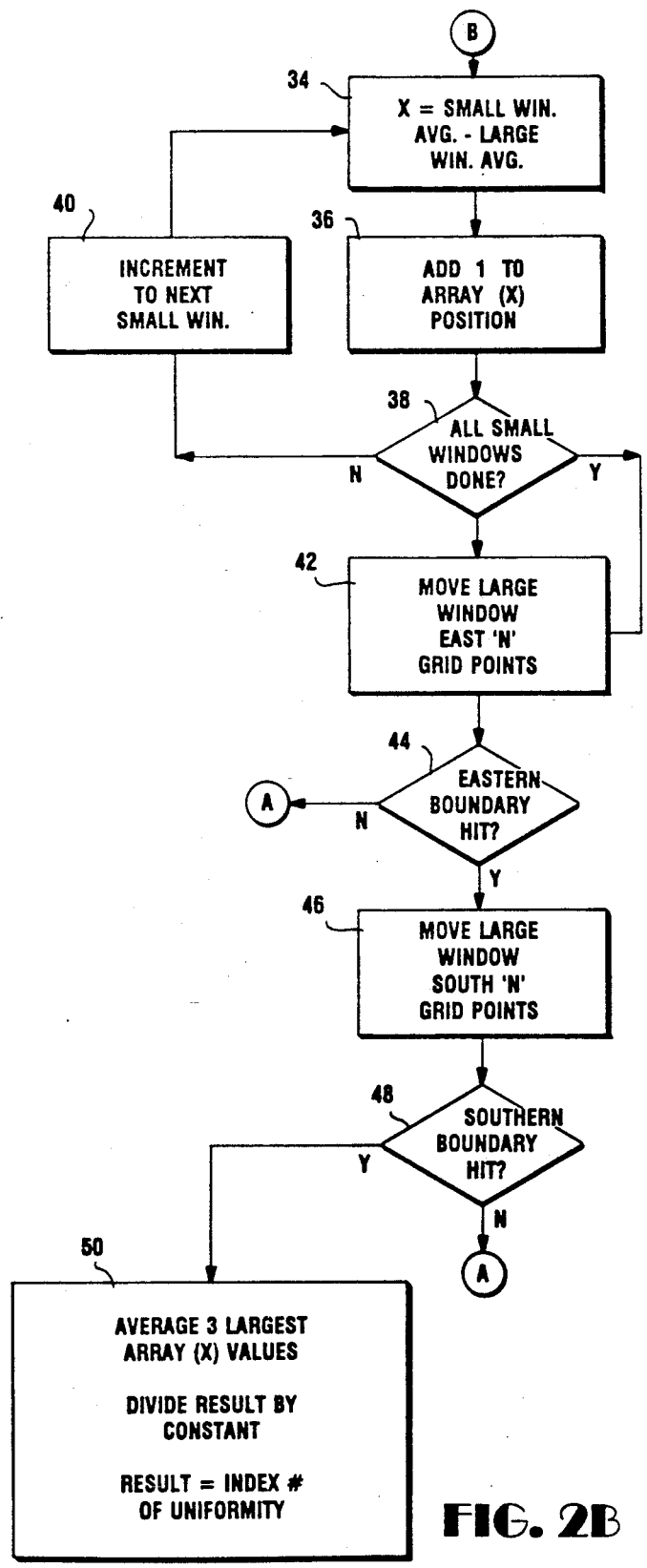

FIGS. 2A and 2B are a flowchart depicting in further detail the processing of the compensated paper sample image. A formation number is obtained by uniquely processing the compensated image data by analyzing the relative intensities of blocks of pixels having a predetermined length in the X and Y directions with respect to smaller inner blocks of pixels in a manner which will be explained in detail below.

In general, the flowchart of FIGS. 2A and 2B show that the grey level intensity of surrounding pixels is obtained by averaging the intensity of all the pixels within a large box. Thereafter, the grey level of each pixel within the large box is subtracted from the average grey level of a small box. This difference is scaled using a scaling factor such that it points to a specific bin in a 64 bin histogram. Finally, the bin to which the scaled difference points is incremented when all the pixels within a larger box have been processed. The larger box window pointer is incremented to point to a new large box. When the entire image has been analyzed, a formation index is computed by adding up the three largest bins and computing their average. The average is divided by a scaling factor to scale the index down so that the index range is between 19 and 122. In essence, a standard deviation is taken of the constructed histogram.

Turning to the flowchart of FIG. 2A, initially, the compensated image input data is generated as indicated above and is utilized as the input data (20) for the present routine. It is noted that this routine is designed to express the uniformity of any two-dimensional set of datum which represents some phenomenon as a single numerical value.

As indicated as block 22, the data is divided so as to form a grid of rows and columns defining a two-dimensional array of small spatial areas. Each spatial area of the grid may be uniquely addressed by its row and column. The spatial area contains a numeric value representing some unique quantity of the phenomenon being examined.

Figure 3:
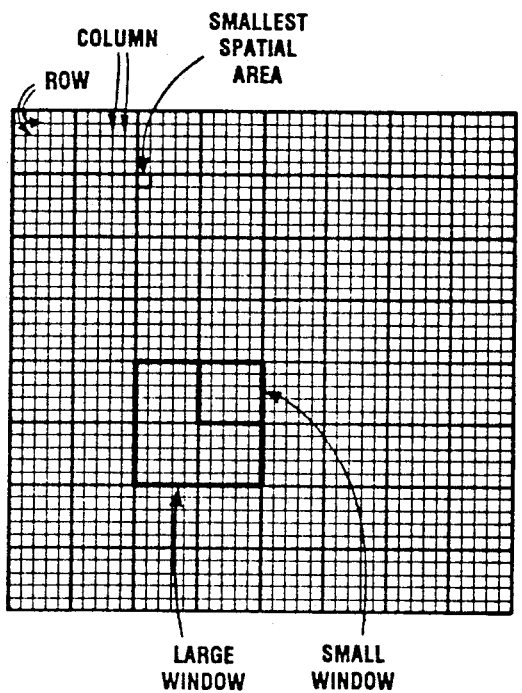
FIGS. 3-6 are grids of rows and columns illustrating the manner in which large and small windows are utilized in the processing described in conjunction with FIGS. 2A and 2B.

FIG. 3 shows a grid of such rows and columns. The smallest spatial area of the grid identified in FIG. 3 is a picture element or pixel. In the present exemplary embodiment, each picture element is represented by two pieces of information, i.e., its location in the grid and its intensity level. As noted above, the scale of intensity level ranges from 0 for black to 255 for white. These grey levels are separated by a sensitivity of 0.017578 volts per grey level by the frame grabber board 4. The size of the spatial areas defined by the rows and columns remain constant for the entire process.

Thereafter, a large window such as that shown in FIG. 3 is created consisting of some multiple of rows and column so as to be evenly divided into the grid created in block 22 (24). It is noted that the large window can be any desired size as long as it is integrally divided by the number of pixels.

Having defined a large window at block 24, the large window is positioned into the northwest corner of the grid of datum that had been created at block 22 (26).

Figure 4:
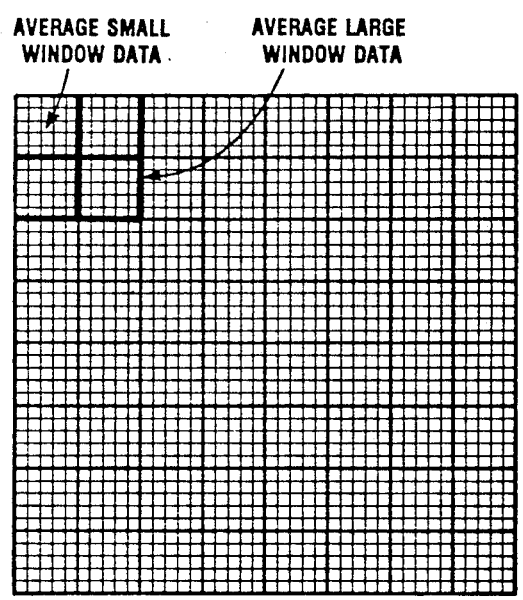

Thereafter, as shown in FIGS. 3 and 4, the large window is subdivided into smaller windows such that the smaller windows are integrally divisible into the larger one (28). The size of the smaller windows remain constant during the remainder of the execution of the subroutine.

Thereafter, the relative intensity of each of the data points in the large window is summed and divided by the number of data points to determine the average intensity level of all the data points in the large window (30). By way of example only, assuming a 512 by 512 grid, if the large window is defined by 36 pixels by 36 pixels, then the intensity level of each of these data points is summed and divided by the total number of pixels.

The average intensity value of the smaller windows (which may, for example, be defined by 6 pixels by 6 pixels) is then similarly determined by adding the intensity level of each data point enclosed within a smaller window and dividing by the total number of data points in a smaller window (32). As shown in FIG. 4, there may be 4 small windows in a larger window.

As indicated at block 34, each small window intensity average is subtracted from the large window average and each difference value X goes into an interval or bin in a histogram. Thus, for a first of the four small windows contained in the larger window shown in FIG. 4, the average intensity value of the large window is subtracted from the average value of the small window and the resulting value is tabulated in an array. The result is then scaled by a constant and offset value to yield a result that can be represented in histogram format.

After the large window average in the northwest corner of the grid is subtracted from the first small window average and stored in a first position in an array X as indicated at 34, then one is added to the array X position pointer to move to the next position in array X (36). Thereafter, a check is made at block 38 to determine whether all the small windows in the larger window have been processed. If not, then the routine is incremented such that the next small window intensity level average is accessed (40) so that the large window average may be subtracted from the next small window average in accordance with block 34.

Figure 5:
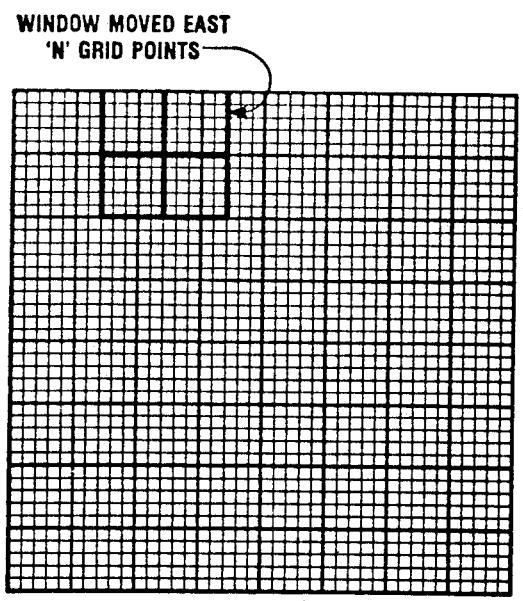

Upon the completion of all small windows in the large window as indicated by the test at block 38, the large window will be moved east as shown in FIG. 5, a selectable number of columns so as to overlap the previous window position by a user selectable percentage (which should be integrally divisible into the grid of data). For example, if the large window is 36 pixels by 36 pixels, the move step indicated at 42 might involve moving the larger window 27 columns to create a 9 pixel overlap with the first large window.

Thereafter, a check is made to determine whether the eastern movement of the large window has resulted in hitting the eastern boundary of the grid (44). If not, then the process is repeated by branching back to block 30, where the average intensity of the new large window is calculated followed by the execution of blocks 32 through 40, thereby resulting in further difference values which indicate the histogram bins which are to be incremented.

Figure 6:
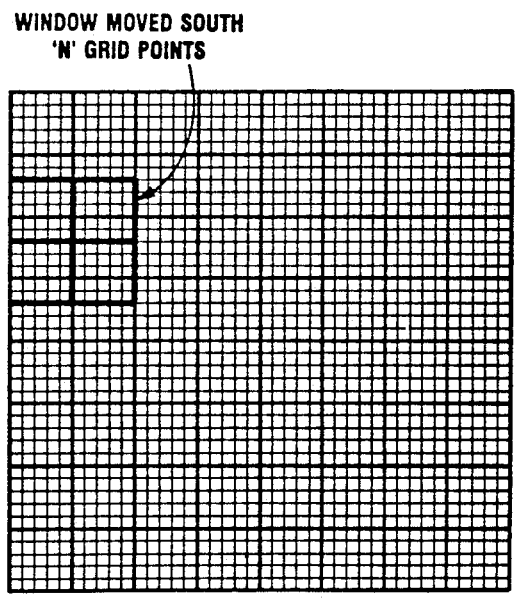

When the check at block 44 indicates that the eastern boundary is hit by the new large window, then the routine returns to the western boundary of the grid but moves south a number of rows so as overlap the previous rows position by a user selectable amount (which is integrally divisible into the grid of data) as is shown in FIG. 6 (46) In this regard, if the large window is 36 by 36 pixels, then the large window may be moved south, for example, by 27 rows.

As indicated at 48, a check is then made to determine whether the southern boundary is hit. If not, the routine branches back to block 30 thereby resulting in a repetition of the above described processing steps and resulting in the window moving east again, repeating the southward movement each time the eastern boundary is encountered. It is noted that the values of these increments, in the eastern or southern direction, are chosen at the onset of the process and remain constant for the entire process. The difference data discussed above with regard to block 34 is calculated for each of the newly defined large windows and as noted above such resultant values indicate the histogram bin to increment. This process is repeated until the entire grid of data has been covered. Once the check at block 48 indicates that the southern boundary has been hit, then the entire grid of data will have been covered.

After all the histogram data has been accumulated, the array of data values is scanned. The three highest quantity intervals of the histogram are then determined. These stored values are then averaged from these three highest quantity bins and divided by a constant to yield an indicator of the uniformity of the overall data. The result is equal to the index of the uniformity of the sample (50). The higher this index, the more uniform the data and the lower the value, the lower uniformity of the sample. As noted above, the index and value generated by this process varies from approximately 19 to 122. The actual index value resulted from dividing the average of the three largest quantity bins by a constant. This constant which by way of example only, was 90, may be any convenient value depending upon the size of the scale that is desired.

The flow of control delineated by the flowcharts shown in 2A and 2B may be implemented by a wide variety of computer programs. An exemplary routine for implementing the flowchart of FIGS. 2A and 2B is appended hereto as appendix A.

As indicated above, the user may select one of three exemplary formats defining how the formation test results are printed. In this regard, by way of example only, by hitting the index switch 19, the user can initiate the generation of a report showing a formation index for each the of different positions of the sample tested with the average, minimum, and maximum formation indices also being printed. By hitting the profile switch 23, the user can generate a printed profile report showing tests statistics including a graphic profile of paper formation data indicating the formation index for each position tested.

Figure 7:
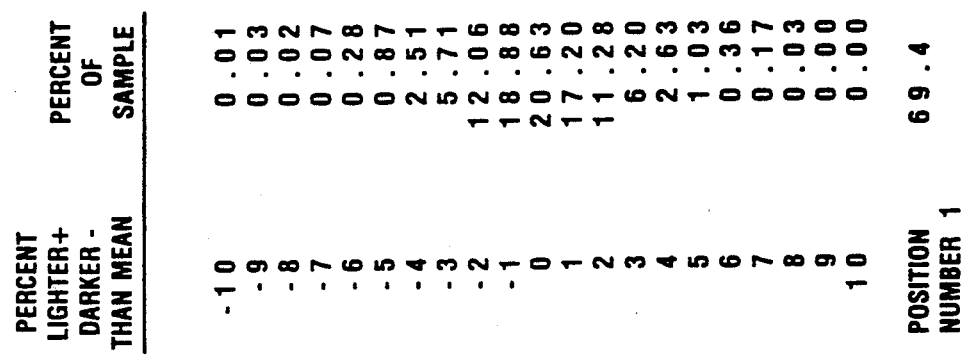
FIG. 7 is an exemplary histogram illustrating the formation index related data that may be generated in accordance with the present invention.

Finally, if desired, the user by hitting the histogram switch 21 can initiate the generation of a histogram such as shown in FIG. 7. The histogram report shows the above-described difference information in the form of percentage of sample area and intensity variation darker or lighter from a mean value. Thus, as shown in FIG. 7, the percentage plus or minus 10 percent lighter or darker than the mean is shown together with the percentage of the sample falling within the associated percent.

It is noted that the higher percentage of the sample area that is closer to the mean the better the formation, and vice versa. More bins filled farther away from the mean indicates larger gradient changes within the sheet.

The histogram shown in FIG. 7 includes well over 70% of the sample within 2% of the mean. The sample has a format index as shown in FIG. 7 of 69.4. It is noted that if the histogram data showed several bins for example as low as 30% darker than the mean, such data may indicate dirt or other significant disturbances. Similar numbers on the lighter than the mean side may indicate pin holes on a sample sheet. The histogram shown in FIG. 7 is data from a sample area of six square inch and represents a first position test of the sample.

```
/*****************************************************************/
/*                    Quick formation                            */
/*                                                               */
/*                                                               */
/*                                                               */
/*                                                               */
/*                  110 volt 60 hertz version                    */
/* The formation number is computed by analysis of the relative intensities */
/* of blocks of superpixels with respect to smaller, inner superpixels. */
/* The size of the superpixels is controlled by the input variables, */
/* SMXBOXSIZE and SMYBOXSIZE, where SMXBOXSIZE determines the superpixels */
/* length in pixels in the x direction and similarly, SMYBOXSIZE determines */
/* the length in the y direction. The gray level intensity of surrounding */
/* pixels is obtained by averaging the intensity of all the superpixels */
/* within a larger box, whose size is dictated by LGXBOXSIZE and */
/* LGYBOXSIZE.                                                   */
/* Then the gray level of each superpixel within the larger box is */
/* subtracted from the average gray level of the larger box. This difference */
/* is next scaled using the scaling factor SCALING so that it points to a */
/* specific bin in a 64-bin histogram. Finally the bin to which the scaled */
/* difference points is incremented. When all the superpixels within the */
/* larger box have been processed in this manner, the larger box is incremen- */
/* ted to point to a new large box. LGXBOXINC and LGYBOXINC control the */
/* incrementing of the larger box through the image. When the entire image */
/* has been anaylzed, a formation index is computed by adding up the three */
/* largest bins and computing their average. We then divide this number by 10 */
/* then divide this number by 3 to scale our number down so that the range is */
/* from 25 to 120. In essence we have taken out much of the error involved by */
/* simply dividing the height by the width.                      */
/*                                                               */
/*                    WARNING !!!!!!                             */
/*                                                               */
/*   This module should not be changed in any way because even slight */
/* modifications can drastically change the formation results. Make sure that */
/* you are aware of what you are doing if you decide that this module needs to */
/* be changed. You had better check with someone else before changing any part */
/* of this module.                                               */
/*                                                               */
```

```
/***********************************************************************/
/*                      VARIABLE DICTIONARY                            */
/*                                                                     */
/* boxnumber     -loop counter of the number of small boxes            */
/* bmax          -the average of the largest three bins of the histogram */
/* bmax1         -the largest bin's number                             */
/* bmax2         -the second to largest bin's number                   */
/* bmax3         - the third to largest bin's number                   */
/* densitydif    -average intensity of the small box - average intensity of the */
/*                large box                                            */
/* form2         -the formation number that is computed                */
/* histo         -the histogram of the formation number that we pass back */
/* lgboxarea     -the area of the large boxes                          */
/* lgboxmean     -the mean average of the large box                    */
/* lgboxsum      -the running sum of largebox as determined by the small boxes */
/* lgxboxinc     -size of the large box increment in the x direction   */
/* lgxboxsize    -size of the larger outside box in the x direction    */
/* lgxdirection  -for loop counter x direction of large boxes incremented */
/*                by lgxdirection                                      */
/* lgxtem        -the largest x-direction location in which we will increment */
/*                by lgxboxsize                                        */
/* lgyboxinc     -size of the large box increment in the y direction   */
/* lgyboxsize    -size of the larger outside box in the y direction    */
/* lgydirbx      -starting location of the large box in the y-direction */
/* lgydirection  -for loop counter y direction of large boxes incremented */
/*                by lgydirection                                      */
/* lgytem        -the largest y-direction location in which we will increment */
/*                by lgyboxsize                                        */
/* numtests      -the number of the current test being taken  (-1)     */
/* scaling       -the scaling factor for the bins                      */
/* smboxarea     -the area of the small boxes                          */
/* smboxesinlgbox -the number of smaller boxes in one large box        */
/* smboxmean     -the mean average of the small box                    */
/* smxboxsize    -size of the small inner box in the x direction       */
/* smborsums     -array of the sum of the small boxes                  */
/* smxdirection  -for loop counter x direction of small boxes inside the */
/*                large box incremented by smxboxsize                  */
/* smyboxsize    -size of the small inner box in the y direction       */
/* smydirection  -for loop counter y direction of small boxes inside the */
/*                large box incremented by smyboxsize                  */
/* temp          -form   array of numbers                              */
/* bin           -for    counters                                      */
/* xdirbox       -the ending location of the large box in the x direction */
/*                                                       CJ 2/25/87    */
/*                      UPDATES                                        */
/*                                                                     */
/* 8/19/87  CJ   changes marked after this date modulation complete    */
/* 9/03/87  CJ   parameters passed temp & histo                        */
/* 12/20/87 CJ   warning documentation typed in                        */
/* 1/18/87  CJ   changed formation to use mean of blocks for speed     */
/* 3/29/88  CJ   put in rounding of formation number to the tenths place */
/* 3/30/88  CJ JM changed routine so that it runs in 16 seconds  orsum */
/***********************************************************************/
#include "declare_test.h"
#define EU 0x014
rotoformation(lgxboxsize,lgyboxsize,smxboxsize,smyboxsize,
lgxboxinc,lgyboxinc,scaling,temp,histo,numtests)

int lgxboxsize,lgyboxsize,smxboxsize,smyboxsize,lgxboxinc,lgyboxinc,*histo,*numtests;
float scaling,*temp;

{
  int    lgydirection,lgxdirection,smydirection,smxdirection,bin,xdirbox;
  int    smboxesinlgbox,lgxtem,lgytem,lgydirbx;
  float  smboxarea,lgboxarea;
  int    bmax1,bmax2,bmax3,boxnumber;
  float  form2,bmax,lgboxmean,smboxmean,densitydif;
  long   lgboxsum,smboxsums[500];

lgboxarea=(float)(lgxboxsize*lgyboxsize);
  smboxarea=(float)(smxboxsize*smyboxsize);   /* Get area of small box.  */
  smboxesinlgbox=(lgyboxsize*lgxboxsize)/(smyboxsize*smxboxsize);
  lgxtem=512-lgxboxsize;
  lgytem=480-lgyboxsize;
```

```
for (bin=0;bin<64;bin++)         /* Clear the histogram.              */
    *(histo+bin)=0;

for (lgydirection=5;lgydirection<lgytem;lgydirection+=lgyboxinc)
    {                            /* Control placement of larger box.  */
    lgydirbx=lgydirection+lgyboxsize;
    for (lgxdirection=5;lgxdirection<lgxtem;lgxdirection+=lgxboxinc)
        {
        xdirbox=lgxdirection+lgxboxsize;
        boxnumber=lgboxsum=0;
        for (smydirection=lgydirection;smydirection<lgydirbx;smydirection+=smyboxsize)
                                 /* Get each small box within larger box.  */
            {
            for (smxdirection=lgxdirection;smxdirection<xdirbox;smxdirection+=smxboxsize)
                                 /* control the x direction of the small box  */
                {
                grsum(&smboxsums[boxnumber],smxdirection,smydirection,
                      smxboxsize,smyboxsize,1);
                lgboxsum+=smboxsums[boxnumber];
                boxnumber++;
                }
            }
        lgboxmean=lgboxsum/lgboxarea;
        for (boxnumber=0;boxnumber<smboxesinlgbox;boxnumber++)
            {
            smboxmean=smboxsums[boxnumber]/smboxarea;
            densitydif=smboxmean-lgboxmean;
            bin=(int)((densitydif*scaling)+32.5);
            if (bin>=0 && bin<65)
                *(histo+bin)=*(histo+bin)+1;
            }
        }
    }
bmax1=0;
bmax2=0;
bmax3=0;
for (bin=0;bin<64;bin++)
    {                            /* Find peak three bins of the histogram.  */
    if (*(histo+bin)>bmax1)
        {
        bmax3=bmax2;
        bmax2=bmax1;
        bmax1=*(histo+bin);
        }
    if (*(histo+bin)>bmax2)
        {
        bmax3=bmax2;
        bmax2=*(histo+bin);
        }
    else if (*(histo+bin)>bmax3)
        bmax3=*(histo+bin);
    } bmax=(bmax1+bmax2+bmax3)/(float)(3);    /* compute the average of the three  */ form2=(float)(((bmax))/((float)(10.0))); /* compute fixed base form.   */
form2=form2/(float)(3.0);               /* scale down the result so that     */
                                        /* our formation numbers are between */
                                        /* 25 and 120                        */ retform2:

form2=form2*100;          /* multiply number by 100 to move decimal   */
form2=(int)form2;         /* truncate the number                      */
form2=form2+5;            /* add 5 to round up the tenths place       */
form2=form2/10;           /* divide by 10 to get rid of 100 ths place */
form2=(int)(form2);
form2=form2/10;           /* divide by ten to put back rounded tenths */

*(temp+*numtests)=form2;  /* set the appropriate element of the array */
}
```

While invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for determining the uniformity of a medium comprising the steps of:
    illuminating said medium by transmitting light through the medium;
    generating digital data corresponding to the intensity level of data points in a two dimensional array of data points on said illuminated medium;
    dividing said digital data into a plurality of relatively large two dimensional windows;
    subdividing each of said large windows into a plurality of smaller windows;
    determining the average intensity of the data points in at least one large window;
    determining the average intensity of he data points in at least one of the smaller windows within the associated large window;
    determining the difference in the average intensity level between at least one smaller window and its associated large window; and
    generating an index representing the uniformity of said data as a function of the difference in intensity levels between data points in said at least one of the smaller windows and its associated large window.

2. A method according to claim 1, wherein said step of illuminating includes the step of varying the illumination until the mean intensity of the illuminated medium is at a predetermined level.

3. A method according to claim 2, wherein said step of varying includes the step of controllably varying the voltage applied to the light source illuminating said medium until said predetermined level is reached.

4. A method according to claim 1, wherein the step of illuminating includes the step of interposing diffusing material between a light source and said medium to create a diffuse light source.

5. A method according to claim 4, wherein said step of interposing includes the step of disposing two levels of diffusing material between said light source and said medium.

6. A method according to claim 1, wherein said step of dividing said digital data into a plurality of windows includes the step of defining a set of overlapping windows.

7. A method according to claim 1, further including the step of storing the difference between said large window average intensity and said smaller window average intensity for a plurality of windows; and
    organizing the average intensity difference values into a set of difference value storage bins.

8. A method according to claim 7, further including generating said index based on the values in a predetermined number of selected storage bins.

9. A method according to claim 8, wherein said selected storage bins include the highest quantities of difference values.

10. A method for determining the uniformity of a medium comprising the steps of:
    illuminating said medium;
    generating digital data corresponding to the intensity level of data points in a two dimensional array of data points on said illuminated medium;
    dividing said digital data into a plurality of two dimensional windows;
    generating an index representing the uniformity of said data as a function of the intensity levels in a plurality of said two dimensional windows;
    wherein said step of dividing includes the step of dividing said digital data into a plurality of relatively large two dimensional windows and subdividing each of said relatively large windows into a plurality of smaller windows;
    determining the average intensity of the data points in at least one large window, and determining the average intensity of the data points in at least one of the smaller windows within the large window;
    storing the difference between said large window average intensity and said smaller window average intensity for a plurality of windows;
    organizing the average intensity difference value into a set of difference value storage bins; and
    generating said index based on the values in a predetermined number of selected storage bins, wherein said selected storage bins include the highest quantities of difference values and wherein said step of generating an index includes the step of averaging the intensity values of the predetermined number of selected storage bins and dividing said average value by a predetermined constant.

11. A method for determining the uniformity of a medium comprising the steps of:
    illuminating said medium by transmitting light through the medium;
    generating digital data corresponding to the intensity level of data points in a two dimensional array of data points on said illuminated medium;
    dividing said digital data into a plurality of large two dimensional windows;
    subdividing each of said plurality of large two dimensional windows into a plurality of smaller windows;
    generating an index representing the uniformity of said data as a function of the difference in intensity levels between data points in at least one of said smaller windows and its associated large window;
    wherein said step of generating said index includes:
    determining the uniformity of the background illumination prior to illuminating the medium to be tested;
    storing data relating to said background illumination; and
    compensating said generated digital data relating to said illuminated medium based on said stored background illumination data.

12. A method according to claim 1, wherein said medium is paper.

13. A method according to claim 12, further including the step of determining whether said paper is fit for a predetermined purpose based on said generated index.

14. Apparatus for determining the uniformity of a medium comprising:
    means for illuminating said medium by transmitting light through the medium;
    means for generating digital data corresponding to the intensity level of data points in a two dimensional array of data points on said illuminated medium;

means for dividing said digital data into a plurality of relatively large two dimensional windows and for subdividing each relatively large window into a plurality of smaller windows;

means for determining the average intensity of the data points in at least one large window and for determining the average intensity of the data points in at least one of the smaller windows within the associated large window;

means for determining the difference in the average intensity level between at least one smaller window and its associated large window; and means for generating an index representing the uniformity of said data as a function of the difference in intensity levels between data points in said at least one of the smaller windows and its associated large window.

15. Apparatus according to claim 14, wherein the means for illuminating includes means for varying the illumination until the mean intensity of the illuminated medium is at a predetermined level.

16. Apparatus according to claim 15, wherein said means for varying includes variable power supply means for generating a variable output voltage and means for controllably varying the output voltage from said power supply means applied to the light source until said predetermined level is reached.

17. Apparatus according to claim 16 wherein said means for illuminating includes diffusing material interposed between a light source and said medium to create a diffuse light source.

18. Apparatus according to claim 17, wherein said diffusing material includes two spaced apart levels of diffusing material between said light source and said medium.

19. Apparatus according to claim 14, wherein said means for dividing said digital data into a plurality of windows includes means for defining a set of overlapping windows.

20. Apparatus according to claim 19, further including means for storing the difference between said large window average intensity and said smaller window average intensity for each of a plurality of window; and means for organizing the average intensity difference values into a set of difference value storage bins.

21. Apparatus according to claim 20, wherein said index is based on the values in a predetermined number of selected storage bins.

22. Apparatus according to claim 21, wherein said selected storage bins include the highest quantities of difference values.

23. Apparatus for determining the uniformity of a medium comprising:

means for illuminating said medium;

means for generating digital data corresponding to the intensity level of data points in a two dimensional array of data points on said illuminated medium;

means for dividing said digital data into a plurality of relatively large two dimensional windows and for subdividing each relatively large window into a plurality of smaller windows;

means for generating an index representing the uniformity of said data as a function of the intensity levels in a plurality of said two dimensional windows;

wherein said means for dividing said digital data into a plurality of windows further includes means for defining a set of overlapping windows;

means for determining the average intensity of the data points in at least one large window and for determining the average intensity of the data points in at least one of the smaller windows within the large window;

means for storing the difference between said large window average intensity and said smaller window average intensity for each of a plurality of windows; and means for organizing the average intensity difference values into a set of difference value storage bins;

wherein said index is based on the values in a predetermined number of selected storage bins, wherein said selected storage bins include the highest quantities of difference values; and wherein said means for generating said index includes means for averaging the intensity values of the predetermined number of selected storage bins and dividing the average by a predetermined constant.

24. Apparatus for determining the uniformity of a medium comprising:

means for illuminating said medium by transmitting light through the medium;

means for generating and storing digital data corresponding to the intensity level of data points in a two dimensional array of data points on said illuminated medium;

means for dividing said digital data into a plurality of large two dimensional windows, said means for dividing including means for subdividing each of said plurality of large windows into a plurality of smaller windows;

means for generating an index representing the uniformity of said data as a function of the difference in intensity levels between data points in at least one of said smaller windows and its associated large window; said means for generating an index further including:

means for determining the uniformity of the background illumination prior to illuminating the medium to be measured;

means for storing a two dimensional reference image of data relating to said background illumination; and means for compensating said generated digital data relating to said illuminated medium based on the differences of said stored background illumination data and said generated digital data.

25. A method for determining the uniformity of the physical distribution of solid constituents forming a medium comprising the steps of:

obtaining digital data indicative of the physical distribution of solid constituents forming said medium;

dividing said digital data into a plurality of relatively large two dimensional windows;

subdividing each of said large two dimensional windows into smaller windows; and generating an index representing the uniformity of said data as a function of the difference between the average of the data in at least one of said large two dimensional windows and the average of data in at least one associated smaller windows.

26. A method according to claim 25, wherein said step of dividing said digital data into a plurality of windows includes the step of defining a set of overlapping windows.

27. A method according to claim 25, further including the step of storing the difference between said large window average and said smaller window average for a plurality of windows; and organizing the average difference values into a set of difference value storage bins.

28. A method according to claim 27. further including generating said index based on the values in a predetermined number of selected storage bins.

29. A method according to claim 28. wherein said selected storage bins include the highest quantities of values.

30. A method for determining the uniformity of data representing a predetermined phenomena comprising the steps of:

dividing said digital data into a plurality of relatively large two dimensional windows;

subdividing each of said large two dimensional windows into smaller windows;

generating an index representing the uniformity of said data as a function of the difference between the average of the data in at least one of said large two dimensional windows and the average of data in at least one associated smaller windows;

storing the difference between said large window average and said smaller window average for a plurality of windows: organizing the average difference values into a set of difference value storage bins;

wherein said generated index is based on the values in a predetermined number of selected storage bins, wherein said selected storage bins include the highest quantities of difference values and;

wherein said step of generating an index include the step of averaging the values of the predetermined number of selected storage bins and dividing the average by a predetermined constant.

31. A method according to claim 25, wherein said data represents the intensity levels of a predetermined portion of an illuminated medium.

32. A method according to claim 31, wherein said medium is paper.

* * * * *